US006551344B2

United States Patent
Thill (10) Patent No.: US 6,551,344 B2
(45) Date of Patent: Apr. 22, 2003

(54) SEPTAL DEFECT OCCLUDER (75) Inventor: Gary A. Thill, Vadnais Heights, MN (US)

(73) Assignee: ev3 Inc., Plymouth, MN (US)

( * ) Notice: Subject to any disclaimer, the term of this patent is extended or adjusted under 35 U.S.C. 154(b) by 0 days.

(21) Appl. No.: 09/760,056

(22) Filed: Jan. 12, 2001

(65) Prior Publication Data

US 2001/0037129 A1 Nov. 1, 2001

Related U.S. Application Data (63) Continuation-in-part of application No. 09/558,717, filed on Apr. 26, 2000, now Pat. No. 6,214,029.

(51) Int. Cl.$^7$ ............................................... A61B 17/08
(52) U.S. Cl. ............................................................ 606/213
(58) Field of Search ................................... 606/213, 215

(56) References Cited

U.S. PATENT DOCUMENTS

| | | | |
|---|---|---|---|
| 3,874,388 A | 4/1975 | King et al. ............... 128/334 R |
| 4,007,743 A | 2/1977 | Blake ...................... 128/334 R |
| 4,917,089 A | 4/1990 | Sideris ........................ 606/215 |
| 5,108,420 A | 4/1992 | Marks ......................... 606/213 |
| 5,171,259 A | 12/1992 | Inoue ......................... 606/213 |
| 5,254,133 A | 10/1993 | Seid ........................... 606/215 |
| 5,258,000 A | 11/1993 | Gianturco ................... 606/151 |
| 5,334,217 A | 8/1994 | Das ............................ 606/213 |
| 5,342,393 A | 8/1994 | Stack .......................... 606/213 |
| 5,350,399 A | 9/1994 | Erlebacher et al. ......... 606/213 |
| 5,397,331 A | 3/1995 | Himpens et al. ............ 606/151 |
| 5,425,744 A | 6/1995 | Fagan et al. ................ 606/213 |
| 5,433,727 A | 7/1995 | Sideris ........................ 606/213 |
| 5,507,811 A | 4/1996 | Koike et al. .................. 623/11 |
| 5,634,936 A | 6/1997 | Linden et al. ............... 606/213 |
| 5,709,707 A | 1/1998 | Lock et al. .................. 606/213 |
| 5,725,552 A | 3/1998 | Kotula et al. ............... 606/213 |
| 5,733,294 A | 3/1998 | Forber et al. ................ 606/151 |
| 5,741,297 A | 4/1998 | Simon ......................... 606/213 |
| 5,846,261 A | 12/1998 | Kotula et al. ............... 606/213 |
| 5,853,422 A | 12/1998 | Huebsch et al. ............ 606/213 |
| 5,861,003 A | 1/1999 | Latson et al. ............... 606/213 |
| 5,944,738 A | 8/1999 | Amplatz et al. ............ 606/213 |
| 5,976,174 A | 11/1999 | Ruiz ........................... 606/213 |
| 6,077,291 A | 6/2000 | Das ............................. 606/213 |
| 6,080,182 A | 6/2000 | Shaw et al. .................. 606/213 |
| 6,174,322 B1 * | 1/2001 | Schneit ....................... 606/213 |

FOREIGN PATENT DOCUMENTS

| | | | |
|---|---|---|---|
| EP | 0 474 887 A | 3/1992 | ........... A61B/17/00 |
| WO | WO 95 28885 A | 11/1995 | ........... A61B/17/00 |
| WO | WO 96 32882 A | 10/1996 | ........... A61B/5/00 |

* cited by examiner

Primary Examiner—Gary Jackson
(74) Attorney, Agent, or Firm—Nawrocki, Rooney & Sivertson, P.A.

(57) ABSTRACT

A septal defect occluder is provided having first and second occluder panels. Each occluder panel includes a fabric support structure and fabric suspended therefrom. The occluder panels are conjoined at a plurality of discrete points which are located within an area bounded by each perimeter of the fabric support structures, as well as on the fabric, to thereby form a defect conforming region for the occluder. In an alternate embodiment, each occluder panel includes a cambered fabric support structure and fabric suspended from a perimeter thereof, the occluder panels being arranged in cooperative cambered opposition such that the perimeters of the cambered fabric support structures impart a clamping force upon tissue adjacent a tissue defect interposed there between when the occluder is deployed for tissue defect occlusion.

25 Claims, 9 Drawing Sheets

SEPTAL DEFECT OCCLUDER

CROSS-REFERENCE TO RELATED APPLICATIONS

This application is a continuation-in-part of application Ser. No. 09/558,717, filed Apr. 26, 2000, for SEPTAL DEFECT OCCLUDER. Now U.S. Pat. No. 6,214,029.

TECHNICAL FIELD

The present invention generally relates to devices for occluding septal defects or shunts in the heart or the vascular system, and particularly provides a low profile septal defect conforming device reversibly deliverable via catheter to a septal defect site.

BACKGROUND OF INVENTION

The term "septal defect" generally refers to a perforation or other type hole (i.e., a defect) which passes through a thin wall of muscle or other tissue (i.e., a septum) which divides or separates "areas" within the body. Such defects can occur, either congenitally or by acquisition, between chambers of the heart (i.e., atrium or ventricle) or the great vessels (interatrial and interventricular septal defects or patent ductus arteriosus and aortico-pulmonary window respectively), causing shunting of blood through the opening.

In the case of the atrium, the presence of a significantly large septal defect can allow blood to shunt across the defect from the left atrium to the right atrium and hence on to the left ventricle, aorta and brain. If the defect is not closed, the risk of stroke is increased.

Shunting of blood from the right to the left side can also have negative consequences. This can lead to death due to cardiac failure or hemoptysis.

In patients with significant sized ventricular septal defects or patent ductus arteriosus, there is shunting of blood from the high pressure left ventricle or aorta, into the right side chambers and pulmonary arteries which normally have much lower pressures. The torrential increase in flow at a high pressure can lead to cardiac failure and death, apart from the serious long-term complication of high pulmonary pressures which can cause a reversal of the direction of the shunt.

Atrial septal defects were initially corrected by open heart surgery which required the surgeon to open the chest of a patient and bypass the heart temporarily (e.g., by means of a cardiopulmonary bypass and moderate hypothermia). The surgeon would then physically cut into the heart and suture small defects closed. In the case of larger defects, a patch of a biologically compatible material would be sewn onto the septum to cover (i.e., "patch") the defect.

In order to avoid the morbidity, mortality and long recovery times associated with open heart surgery, a variety of transcatheter closure techniques have been attempted. In such techniques, an occluding device is delivered through a catheter to the septal defect site. Once the closure device is positioned adjacent the defect, it must be attached to the rest of the septum in a manner which permits it to effectively block the passage of blood through the defect.

One such closure device, as illustrated in U.S. Pat. No. 3,874,388 (King et al.), includes a pair of complex mechanical umbrellas, each having a plurality of arms extending radially from a central hub. The hubs of the two umbrellas are mechanically connected to one another and each umbrella includes a fabric covering over the arms, much like a common umbrella. The ends of each arm are provided with barbs which are anchored into the septum to hold the occluder in place. The complex umbrellas prove rather difficult to unfold after passage through a catheter, requiring an array of cables to deploy the arms. This makes proper placement of the device difficult, and the barbs on the arms prevent retraction or repositioning of the device once it is in place. Use of this device has been limited to adult patients because the device requires a large catheter, such as about 23 French (7.3 mm), for delivery.

Rashkind proposed a single-umbrella closure device capable of delivery through a 5 mm system which permitted use in children weighing at least about 20 kg. Similar to the King device, this umbrella utilizes barbed hooks on the ends of umbrella arms to ensure attachment to the septum, with the single umbrella being placed on the left side of the atrial septal defect. The barbs prevent disengagement of the device, and poorly centered or seated devices requiring open heart surgery for correction are common.

Due to the low success rate of previous devices, a "modified double-umbrella Rashkind occluder" in which the arms of the device are hinged to permit them to fold back against themselves was developed. A more compact collapsed condition and a less intrusive delivery as by an 11 French (3.7 mm) catheter were thereby facilitated. Furthermore, such a "clamshell" occluder did not include barbs at the end of the radial arms of the umbrella, allowing it to be readjusted and retrieved. Typically, this could be accomplished only once, and without subsequent redeployment due to damage or destruction of the device. Although arguably an improvement over heretofore known devices, such a device generally requires a complex loading jig for deployment and remains susceptible to moderately high shunting.

Sideris, in U.S. Pat. No. 4,917,089, proposed an occlusion device which combines a single umbrella with a separate anchoring device. Like the previous defect occlusion devices, Sideris' invention utilizes an umbrella with a plurality of radially extending arms. A string connects the arms of this umbrella to a generally rhomboidally shaped anchor which includes an internal wire skeleton and a central, rhomboidally shaped piece of rubber. The string attached to the struts of the umbrella is affixed to the central rubber element of the anchor. The anchor is placed on the opposite side of the septum from the umbrella, and the length of the string limits movement of the occlusion device with respect to the septum. This style of occluder is difficult to deploy, and its overall bulkiness in the heart causes potential clot emboli due to protrusion into the atrial cavities.

Kotula et al., U.S. Pat. No. 5,725,552, provides a collapsible device comprising a heat-set woven metal fabric configured as a bell, hourglass, etc. for occluding an abnormal opening in a body organ. The device of Kotula et al. does not adequately "fill" the defect nor fit flat against, or readily conform to, the structures within the heart, thereby increasing the embolization potential with the use of such device.

Das, U.S. Pat. No. 5,334,217, teaches a non-retrievable occluder having paired disks, each of which comprises a membrane, and an elastically deformable frame carried about the periphery of each membrane. The disks are joined only at central portions of each membrane, thereby defining a conjoint disk. The Das device is intended to be self-centering within the defect. Since the ability to achieve defect conformity is limited due to the defined conjoint disk structure, residual shunting can occur. Furthermore, with such a device, the conjoint disk cannot uniformly apply and distribute a force to the "second" disk (e.g., as when the second disk follows the first disk into the catheter for purposes of retrieval. As a result, the occluder is caused to contort, resulting in non-symmetrical collapse, and the problems associated therewith.

All of the prior art devices described above suffer shortcomings. First, most of these systems (i.e., the occluder and delivery means) are mechanically complex and require a great deal of remote manipulation for deployment or retrieval, if the device is retrievable. This extensive remote manipulation, such as by applying tension to one or more cables in order to deploy the arms of an umbrella or to anchor the device in place, not only increases the difficulty of the procedure, but tends to increase the likelihood that the device will be improperly deployed. This can necessitate retrieval or repositioning so as to effectively occlude the defect in order to minimize the risk of embolization.

Second, all of these devices, except for Kotula and Das, essentially teach two separate members joined to each other at a single interface. With such device, when the left atrial member is opened, the central point tends to ride to the lower margin of the defect. Proper centering of the device is quite difficult, and when a self centering device as disclosed by Das is employed, it is at the cost of defect conformity.

Third, heretofore many known devices have a geometry which tends to prevent the occluder from remaining flat against, or within, the defect once deployed from a catheter, which is in and of itself problematic, and which is likely to deform the tissue adjacent the tissue defect. A further limitation associated with such devices is that intimate contact between the perimeter of the occluder and the tissue adjacent the tissue defect (e.g., a septal wall), a prerequisite for the formation of a smooth endothelial growth layer in the final stages of healing, is difficult to obtain using heretofore known occluders.

Fourth, heretofore many known devices possess retrieval limitations, while others are fully not retrievable.

It is desirable, therefore, to provide a simple, collapsible compact closure device which may be delivered through a catheter. It is also highly advantageous to have such a device which can be readily reversibly deployed and retrieved with a minimum of remote manipulation and applied force. Further, a device which is self-centering and self-occluding, particularly one that possesses a defect conforming variable geometry to fill slit-like defects such as a patent foramen ovale, and one that can be released while still being tethered to the delivery mechanism to assure proper placement and function prior to release, would be superior to heretofore known devices. This is particularly true in view of the need to test for shunting of blood around the occluder device with the septal wall in unrestrained motion prior to release.

SUMMARY OF THE INVENTION

The present invention is a septal defect occluder which has first and second occluder panels. Each occluder panel includes a fabric support structure and fabric suspended from a perimeter thereof. The occluder panels are conjoined at a plurality of points which are located within an area bounded by the perimeter of each fabric support structure, as well as on the fabric, to thereby form a defect conforming region for the occluder.

In an alternate embodiment, a septal defect occluder is provided having first and second occluder panels. Each occluder panel includes a cambered fabric support structure and fabric suspended from a perimeter thereof. The occluder panels are arranged in cooperative cambered opposition such that the perimeters of the cambered fabric support structures impart a clamping force upon tissue adjacent a tissue defect interposed there between when the occluder is deployed for tissue defect occlusion.

The present invention is thus an improved device over structures known in the prior art. More specific features and advantages obtained in view of those features will become apparent with reference to the drawing figures and DETAILED DESCRIPTION OF THE INVENTION.

DETAILED DESCRIPTION OF THE INVENTION

Figure 1:
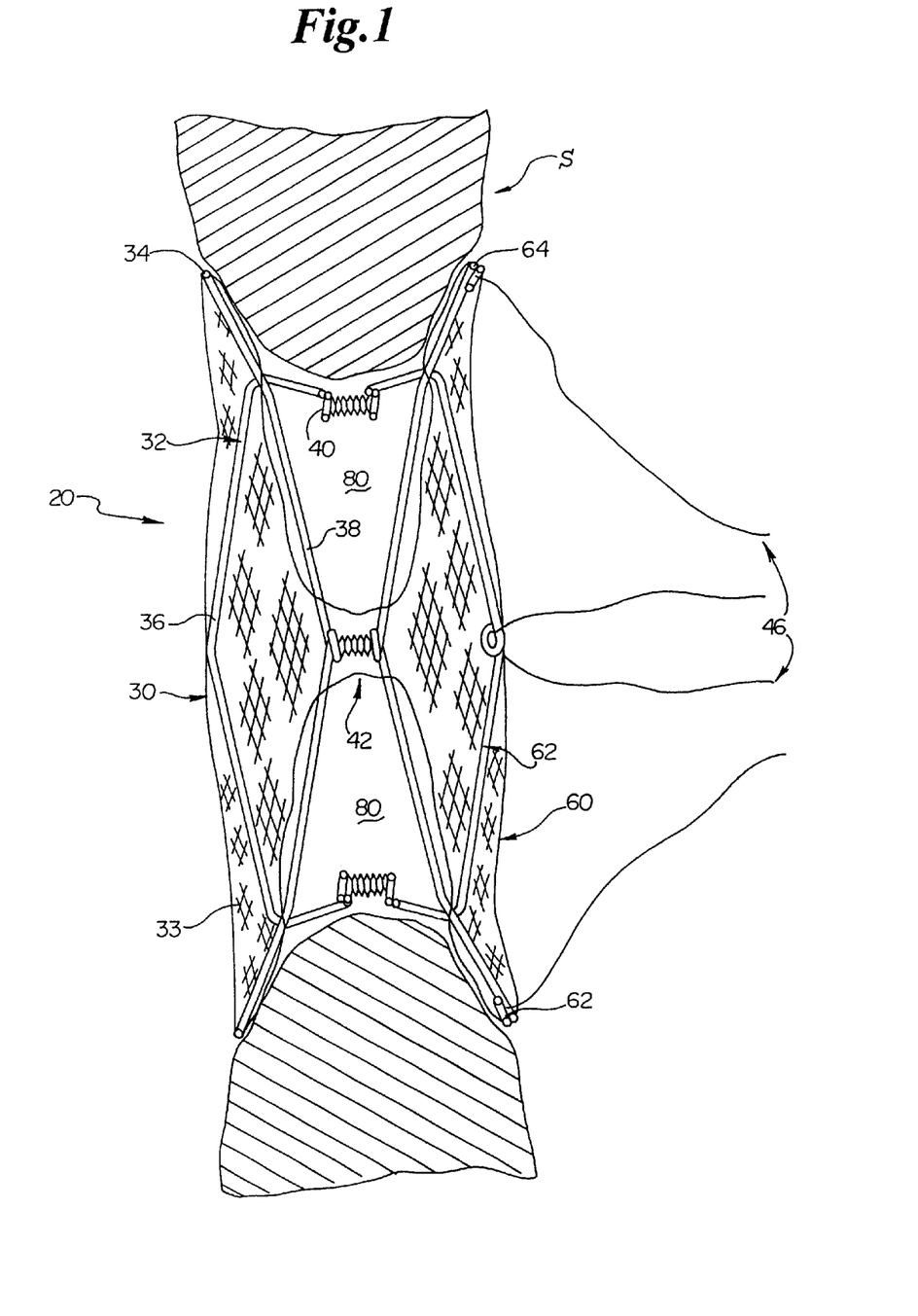
FIG. 1 is a side elevational view of the septal defect occluder of the present invention deployed in a septal defect.

As shown generally in FIG. 1, a septal defect closure device 20 of the invention may be attached to the septum S (e.g., an atrial septum) to effectively conform to and block the defect, without protruding into atrial cavities and the like. As described in detail below, once the closure device 20 is in place, it becomes anchored to the septum and prevents the flow of blood through the atrial septum to the adjoining chambers of the heart. This will permit the heart to operate normally.

Figure 2:
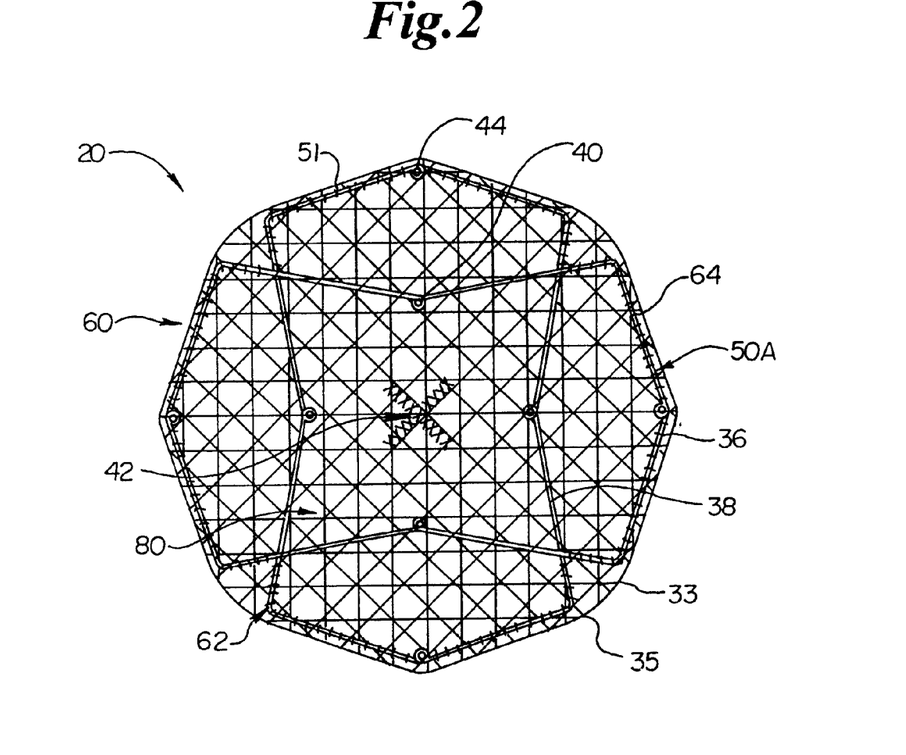
FIG. 2 is an end view of an occluder panel of the septal defect occluder of the present invention, particularly illustrating a center fabric attachment point.

Referring now to FIGS. 1 and 2, the extremely low profile closure device includes first and second occluder panels 30, 60. Each panel 30, 60 is generally round (e.g., circular, oval, elliptical etc.) so as to facilitate positioning, and minimizes chances of erosion and puncture. Each panel 30, 60 generally comprises a fabric support structure 32, 62 and fabric 33 suspended from a perimeter 34, 64 of the fabric support structures 32, 62. The occluder panels 30, 60 are conjoined at a plurality of discrete points, located or positioned within the bounds of each of the fabric support structures 32, 62 (i.e., within an area bounded by each perimeter 34, 64 of the support structures 32, 62), as well as on the fabric 33 (which will be further explained with reference to FIGS. 2, 7 and 8). A defect conforming region 80 for the occluder 20 is thereby formed. The nature (i.e., structure, relationships there between and function) of the defect conforming region will be detailed herein below, particularly with reference to FIGS. 1, 2 and 9–14. At this point it may be said that the region 80 expandingly conforms to substantially completely and thoroughly satisfy the perimeter of the defect geometry. This stabilizes panels 30, 60 so that complete coverage of the defect from either direction is achieved. The defect is thereby occluded without distortion of the defect.

The fabric support structures 32, 62 of the occluder are generally flexible and elastically deformable, and include perimeter and traversing segments 36, 38. Resilient fabric 33 (FIG. 4) is suspended or otherwise affixed to the perimeter segments 36 of the fabric support structures 32, 62. As particularly shown in FIG. 2, the perimeter segments 36 of the fabric support structures 32, 62 extend substantially around the periphery 35 of the fabric 33. The fabric 33 may be formed of a thin, flexible material which can be folded and pulled taut without being damaged. Elastic polymeric materials such as, for example, polyester knit, nylon, polypropylene, polytetrafluoroethylene (e.g., Teflon®), and expanded polytetrafluoroethylene (e.g., GoreTex®), as well as natural fabrics such as silk, are acceptable.

To accommodate the need of the fabric support structure to distort when retrieving the occluder 20 into the catheter, excess fabric can be provided. On an area basis relative to the support structure, an excess of fabric in the range, typically, of about 30–35 percent, and up to 50 percent, is sufficient. This range is required for low stretch fabric that otherwise may prevent the support structure from collapsing in a manner suitable to get into the catheter. However, the 20 denier polyester knit is advantageous in that it is of approximately 50% less bulk than known jersey style knit configurations which facilitates the use of smaller delivery catheters, and allows for the occluders to be retrieved into such catheters at forces that are not detrimental to either the catheter or the occluder (e.g., a 40 mm occluder may be pulled into a 12 French catheter using a reasonable peak force of about four pounds). A further advantage is that two complete fabric "patches" may be incorporated into the closure device (i.e., no need to remove material to reduce bulk), which thereby creates a device having a high reliability of successful closure.

The fabric 33 may be attached to their respective support structures 32, 62 by any suitable means. For instance, the fabric 33 may be directly attached to the support structures 32, 62 by means of an adhesive or the like, or the periphery 35 of the fabric 33 may be wrapped about each of the support structures 32, 62 and the peripheral edge attached to the rest of the fabric so as to essentially define a sleeve about each of the support structures 32, 62. In the latter instance, the sleeve may fit the support structure relatively loosely so that the structure may move within the sleeve with respect to the fabric. The peripheral edge of the fabric may be affixed to the rest of the fabric sheet 33 in any suitable fashion such as by sewing. Preferably, though, the periphery of the fabric can be sewn to at least some portion of the perimeter segments 36 of the support structures 32, 62 using polyester, non-adsorbable suture.

Referring to FIG. 1, the fabric support members 32, 62 of the occluder panels 30, 60 are shown as being spaced from one another for purposes of the present explanation, but this is not the normal configuration (i.e., static condition) of the panels. In a static, non deployed condition, the fabric support structures of the device take a generally planar form, with the two fabric support structures 32, 62 generally abutting against, or closely proximate, one another.

Again referring to FIGS. 1 and 2, the occluder panels 30, 60 are conjoined at a plurality of discrete points, the points being selected to effectively link each of the fabric support structures 32, 62 together, as well as associate each sheet of fabric 33 carried thereby, so as to form the variably configurable defect conforming region 80. With such arrangement, the resilient fabric 33 is not only inherently or indirectly positionable in response to the defect geometry, but also directly responsive vis-a-vis the conjoined support structures 32, 62.

The conjoined points within the fabric support structures 32, 62, which responsively link the opposing structures, comprise loops formed in the traversing segments 38 thereof, these loops defining internal eyelets 40 for the structures 32, 62. The internal eyelets 40 of each of the structures 32, 62 are shown as being joined by suture (e.g., polyester, non-absorbable or other suitable material), and to some extent delimit the defect conforming region 80, and serve to center the occluder 20 within the defect. The remaining points of conjointment comprise the union, at a single point, of the fabric of each of the fabric support structures so as to define a generally central fabric attachment point 42. It is important that fabric 33 of each support structure 32, 62 be limitingly controlled via the union, however it is equally important that the fabric 33 remain substantially suspended for expansion during deployment, preferably exclusively about or by its periphery 35.

As best seen in FIG. 2, the center attachment point 42 of the occluder 20 is preferably but not exclusively configured as a sutured cross stitch positioned in the center of the fabric 33. Other attachment configurations or geometries are contemplated, to the extent that the center attachment point 42 maintains its functionality, namely that of control of the peripherally supported fabric, and generally contributing to a centering function for the occluder. Preferably the internal eyelets 40 are symmetrically oriented about the center fabric attachment point 42.

In addition to internal eyelets 40 which are formed in the traversing segments 38 of each of the fabric support structures 32, 62, the perimeter segments 36 of at least one (i.e., structure 62) of the fabric support structures 32, 62 include loops formed therein, thereby defining perimeter eyelets 44 for that particular support structure 62. As best seen in FIGS. 1 and 8–12, the perimeter eyelets 44 cooperate with urging means 46 carried by and or through a catheter 47 so as to aid in the symmetrical collapse of each of the fabric support structures 32, 62, and the occluder panels 30, 60 thereby, during reversible retrieval of the device 20 into the catheter 47. The perimeter eyelets 44 associated with the "catheter side" occluder panel 60 transmit and distribute deployment and retrieval forces imparted thereupon through the defect conforming region 80 and to the other occluder panel 30. As will subsequently be discussed, the unique configuration of the fabric support structure components, and the relationships there between, provide numerous advantages (for example: symmetrical collapse of the occluder, less peak force for retrieval into a catheter for deployment, and heretofore unsurpassed sealing of narrow slit defects without the distorting effects typically associated with fixed geometry conjoint areas such as circumferential conjoint disks).

Figure 3:
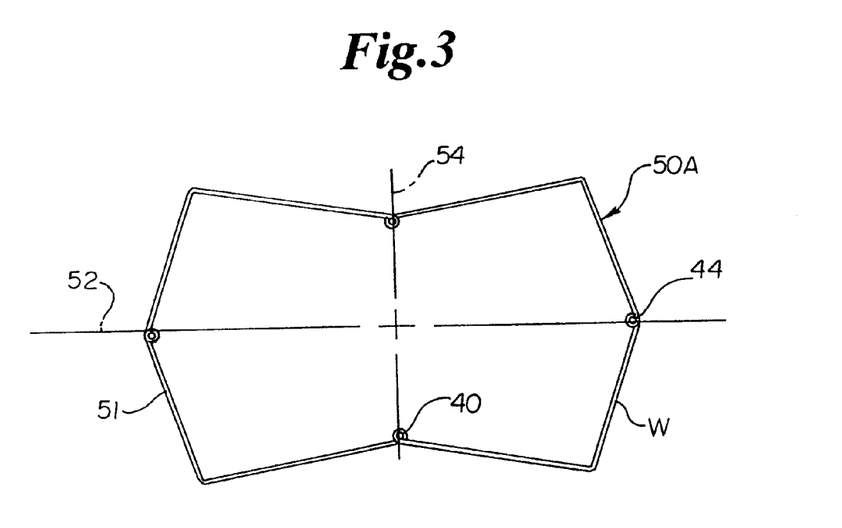
FIG. 3 is an end view of the frame members of the device of the subject invention having two pairs of opposing inward eyelets.

Referring now to FIGS. 3–7, the fabric support structures comprise cooperating frames 50, each of which preferably resembles a "bowtie," as best seen in FIG. 3. A more technical description for the frame geometry might be to characterize it as an octagon (i.e., a frame of eight legs or segments), particularly an octagon having a concave, rather than convex, "top" and "bottom" (i.e., ceiling and floor). Put yet another way, the frames resemble elongated hexagons whose long sides are "pinched" towards each other. The frames 50 may be generally characterized as having maximum and minimum dimensions and corresponding axes of maximum and minimum dimension 52, 54. The above frame description is intended to be illustrative, not limiting, with alternating frame geometries satisfying the general characterization being possible.

The internal eyelets 40 of the fabric support structures 32, 62 are formed in each of the frames 50 along the axis of minimum dimension 54 (FIG. 3), as illustrated. The resilient internal eyelets 40 are generally disposed between adjacent ends of two legs or frame segments 51, one end of the eyelet being attached to each leg 51. The internal eyelets 40 are shown as laying generally in the same plane as the legs 51 and may extend generally outwardly of the periphery of each of the support structures 32, 62, or may preferably extend inwardly of the periphery of the structures as shown in the figures. As will be later discussed with respect to an alternate occluder panel design, each of the frames 50, 50A of the fabric support structures 32, 62 may be cambered about their minimum dimension (i.e., the internal eyelets 40 do not lay in the same plane as the legs 51, or more specifically, the internal eyelets 40 and perimeter eyelets 44 are not coplanar) so as to, among other things, provide an occluder capable of exerting a clamping force at the perimeter edge of the tissue defect when deployed. The eyelets are desirably formed to function as spring hinges. This will serve to ensure that the occluder panels 30, 60, particularly the catheter side panel 60, elastically return substantially to a plane-defining configuration even after they have been collapsed and delivered through a catheter.

Frames 50 of the device have internal eyelets 40, as previously explained. The internal eyelets 40 of one fabric support structure (i.e., 32) mate (i.e., align or register) with those of the other support structure (i.e., 62) so as to thereby conjoin the occluder panels 30, 60 (FIG. 2). The perimeter eyelets 44 of fabric support structure 62 on the other hand are formed in its frames 50A along the axis of maximum dimension 54 (FIG. 3). The perimeter eyelets 44 cooperatively engage urging means 46 so as to enable remote manipulation of the occluder 20 during retrieval.

Figure 5:
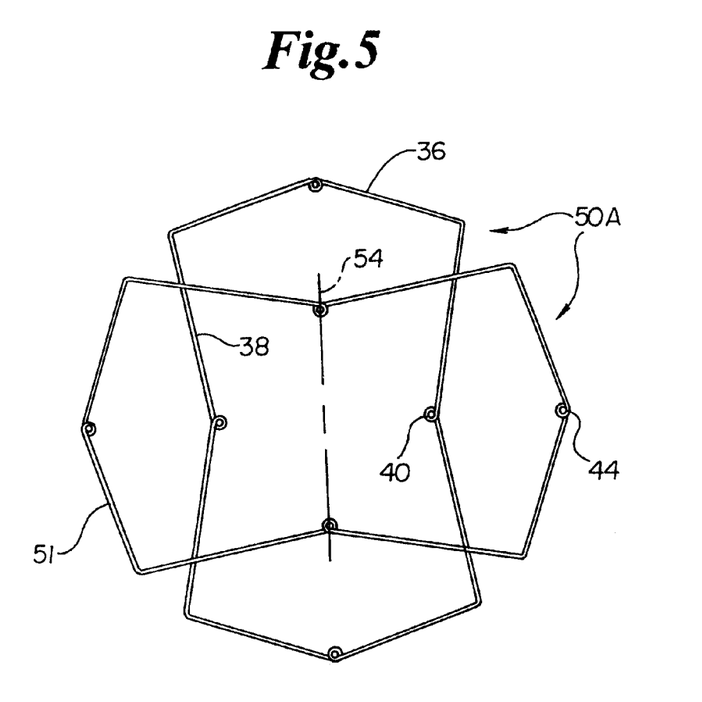
FIG. 5 is an end view of two frame members of FIG. 3 arranged to form a fabric support structure having both internal and perimeter eyelets.
Figure 6:
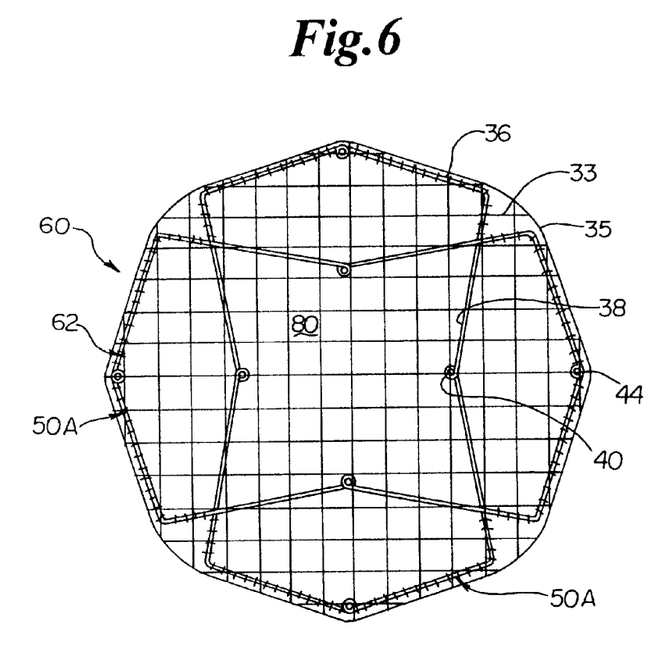
FIG. 6 depicts a first occluder half, corresponding to the fabric support structure of FIG. 5, showing the relationship between the fabric sheet of FIG. 4 and the underlaying support structure.

Each fabric support structure 32, 62 comprises perpendicularly overlaying frames, the axis of maximum dimension 52 of one frame 50 or 50A substantially aligning with the axis of minimum dimension 54 of the other frame (FIG. 5). The somewhat oversized fabric 33 is shown in FIG. 6 underlaying the cooperating frames, the periphery thereof being sewn or otherwise affixed to those portions of the frames, which when configured as shown in FIG. 5, form a perimeter 34, 64 for each of the fabric support structures 32, 62. It is again noted that the preferred fabric 33 contributes to an occluder 20 that has complete opposing fabric patches suspended by the fabric support structures 32, 62, which in turn include a frame geometry and arrangement that generally reduce deployment and retrieval forces. In return, fabric and stitch wear and tear and frame "break through" (i.e., separation of the perimeter segments 36 from the fabric 33 upon expansion of the occluders 30, 60) are minimized.

Each frame 50 is preferably formed of a single elongate strand of wire W. As best seen in FIG. 3, each of the legs 51 may simply comprise a length of the wire, and the wire may be bent through greater than 360 degrees to define adjacent legs 51 and to form the loops or eyelets 40, 44. The ends of the wire may be attached to each other in any secure fashion, such as by means of a weldment or a suitable biocompatible cementitious material.

The frames 50 should be formed of a flexible, elastically deformable material such as a metal, and the wire comprising the frame is formed of a superelastic material. One such material currently known in the art is a near-stoichiometric nickel/titanium alloy, commonly referred to as Nitinol or NiTi. Such superelastic materials may be elastically deformed to a much greater extent than most other materials, yet substantially fully recover their original shape when released. This permits the frame to be deformed sufficiently for insertion into, and passage through, a small-diameter catheter yet automatically elastically return to its initial shape upon exiting the catheter.

Figure 7:
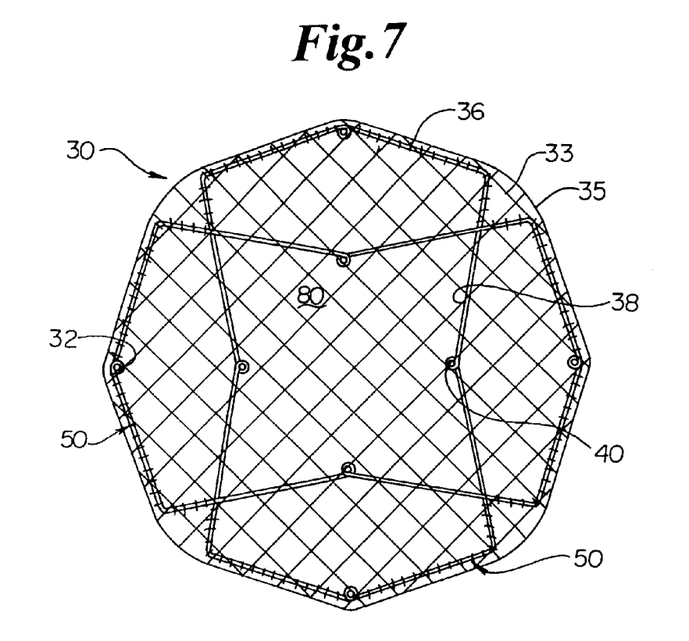
FIG. 7 depicts a second occluder half, corresponding to the second fabric support structure of FIG. 5, showing the relationship between the fabric sheet of FIG. 4 and the underlaying support structure.

The frames are preferably manufactured with nitinol wire that can be wound around the pins of a forming die and subjected to heat treatment. Each device consists of four frames, two frames for each support structure. More particularly, each support structure 32, 62 comprises matchingly paired frame styles (i.e., as shown in FIGS. 6 and 7, occluder panel 30 has a pair of frames 50 whereas occluder panel 60 has a pair of frames 50A). All eyelets 40, 44 can be made having generally a 0.030 inch inside diameter, and, as previously noted, be inward facing (i.e., directed toward the center fabric attachment point 42). The wire ends of each frame can be connected with a titanium hypo tube using a compression crimp. The titanium is more ductile than the nitinol, providing a reliable grip with excellent corrosion resistance. Alternately, the preferred shape of the frame may be cut out from a sheet of such superelastic material as a single block, by chemical etching, punching with a suitable punch and die, or any other appropriate forming method.

In order to enhance radiopacity so that the frame can be viewed remotely during deployment, the frame may be provided with a radiopaque coating, such as gold or platinum. For instance, the wire W may be plated with a thin layer of gold or platinum. In one particularly useful embodiment, a helically wound length of a thin radiopaque wire (not shown) is placed over the wire W; such core/coil structures are well known in the art. Alternatively, radiopaque marking bands (not shown), which are commercially available, may be employed. By placing one such band on each leg of the frame, a physician can remotely visualize the frame as a plurality of small bands; when the bands are appropriately spaced from one another on a monitor, the physician knows that the frame is properly deployed.

Figures 8, 9:
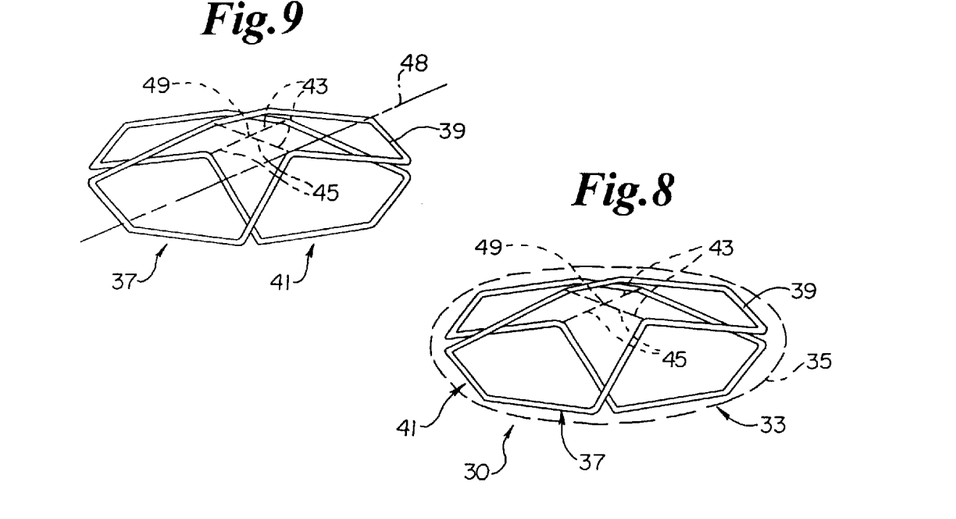
FIG. 8 is an overhead perspective view of an alternate occluder panel.
FIG. 9 is an overhead perspective view of the underlaying cambered fabric support structure of the alternate occluder panel of FIG. 8.
Figure 10:
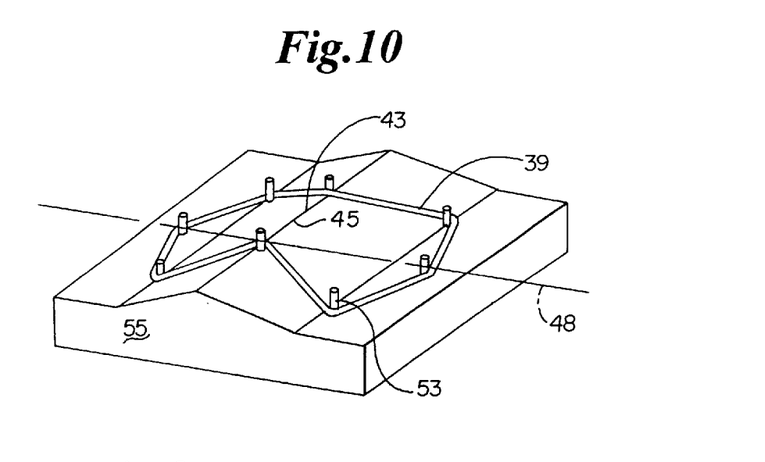
FIG. 10 is an overhead perspective view of a frame member of the cambered fabric support structure being formed using a cambered winding fixture.
Figure 11:
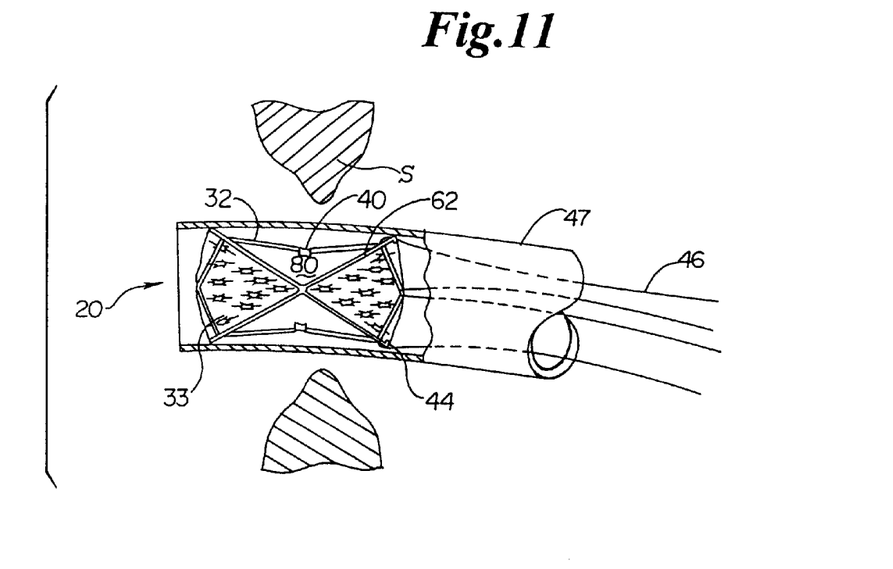
FIG. 11 is a side view of the present invention being delivered within a catheter to a septal defect site.
Figure 12:
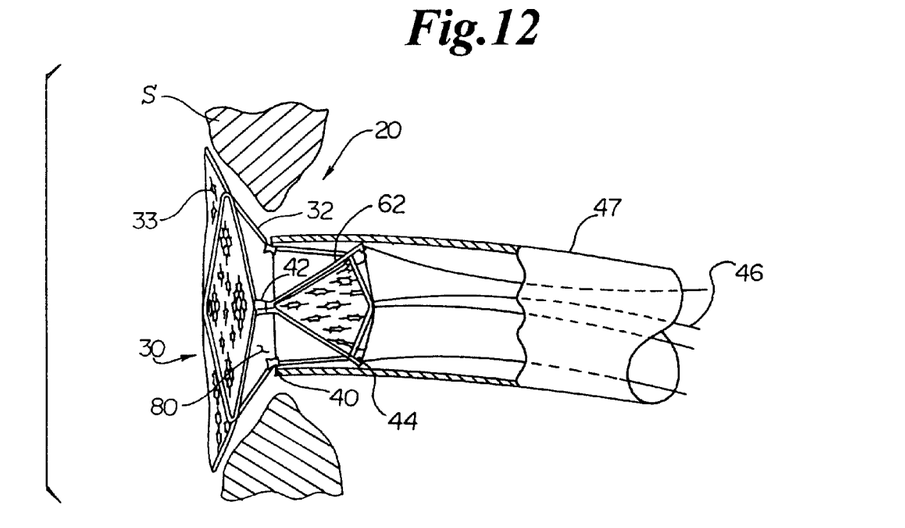
FIG. 12 is a side view of the present invention being initially deployed within the septal defect, the second occluder half having expanded to conform to a portion of the defect.
Figure 13:
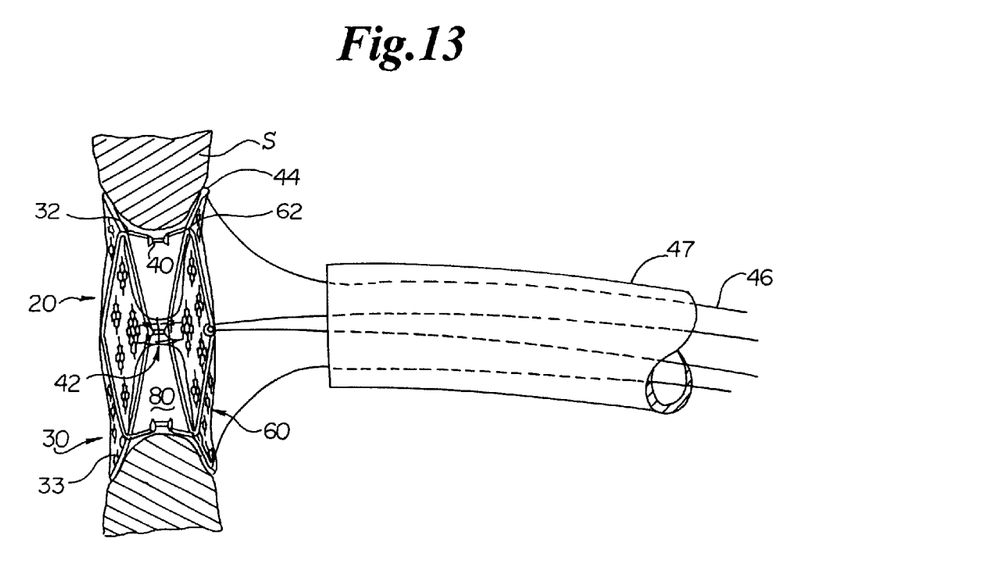
FIG. 13 is a side view of the present invention deployed within the septal defect while under the control of tension imparting means.
Figure 14:
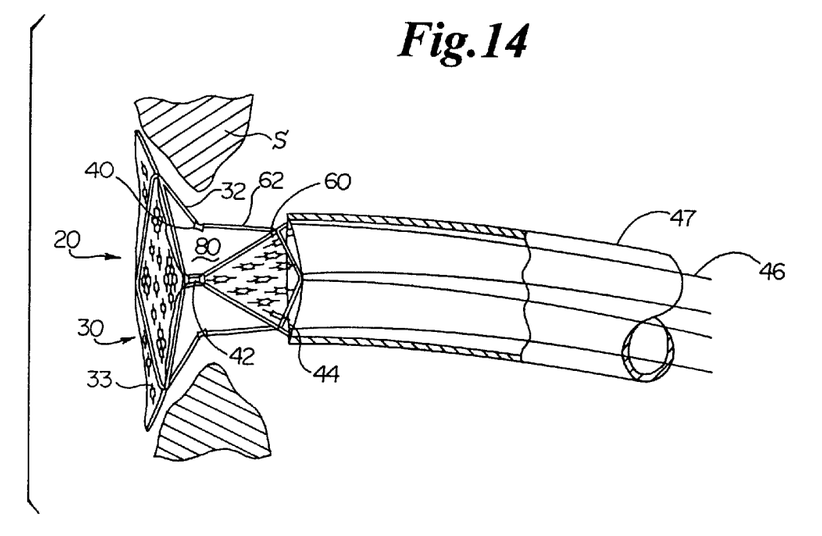
FIG. 14 is a side view of the present invention being initially retrieved into the catheter from the septal defect site, the first occluder half being collapsed for catheter entry; and, FIG. 15 is a side view of the present invention on its way to complete retrieval into the catheter from the septal defect site.
Figure 15:
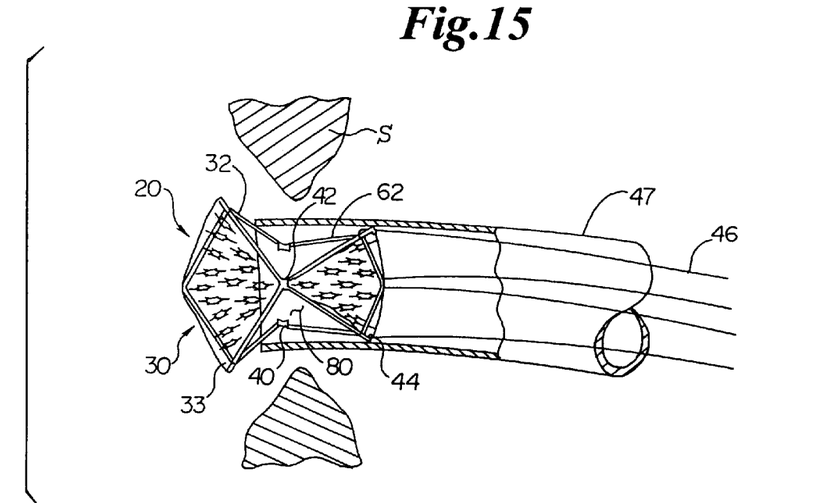

Referring now to FIGS. 8 through 10, an alternate embodiment of the occluder panel 30 (FIG. 8) and, more particularly the fabric support structure 37 (FIG. 9), are shown for the defect occluder of the subject invention. Each occluder panel 30 includes a cambered fabric support structure 37 which otherwise conforms with/to the fabric support structure previously disclosed (i.e., the fabric support structure 37 of FIG. 8, and frame member 39 shown being formed in FIG. 10, each have the general end view appearance as the embodiment depicted in FIGS. 2 and 3 respectively, including eyelets which have been omitted from FIGS. 8 through 10 for the sake of clarity). Each of the occluder panels 30 are arranged in cooperative cambered opposition such that the perimeters 41 of the cambered fabric support structures 37 impart a clamping force upon tissue adjacent a tissue defect interposed there between when the occluder is deployed for tissue defect occlusion. Furthermore, because the entire perimeter 35 of the fabric 33 is supported by the cambered fabric support structure 37, and because the occluder panels 30 are urged together at the perimeter edge of the defect due to their arrangement in biased opposition, intimate contact of the occluder with the tissue is assured which is advantageous in supporting endothelial tissue growth during the final stages of healing.

The aforementioned occluder panel design substantially improves performance in the area of the occluder "go flat" characteristic. Such "go flat" characteristic (i.e., "flatness") is specified as the distance between the perimeter edges of the occluder panels after deployment from the catheter. Heretofore known occluders, particularly larger devices (i.e., in excess of about 28 mm across), sometimes have difficulty returning to a "flat" shape (i.e., less than about 2 mm separation between occluder panels or halves) post deployment from a catheter. Force testing of smaller devices utilizing 0.007" diameter nitinol wire indicated that the return energy of the fabric support structures was far greater than the energy in larger devices utilizing 0.010" diameter nitinol wire, thereby permitting the fabric support structures to substantially overcome the forces associated with the fabric suspended thereover, and thus lay "flat". Solution of the "go flat" problem via an increase in frame wire diameter yielded a less than desirable catheter retrieval force, namely a retrieval force in excess of 5 lbs. Occluder panels having a cambered fabric support structure, and alignment of the panels in biased opposition, provide a tissue defect occluder having a preloaded or added energy effect without increasing wire diameter, and thereby increasing catheter retrieval force.

Each of the frame members or elements 39 of each of the fabric support structures 37 are cambered about their minimum dimension 43 (i.e., the internal eyelets do not lay in the same plane as the legs, or more specifically, the internal eyelets and perimeter eyelets are not coplanar). Said another way, each frame element 39 has a camber axis 45 which is in substantial conformity with the axis of minimum dimension 43, compare FIGS. 3 and 10. Each cambered fabric support structure 37 comprises perpendicularly overlaying frames 39, the axis of maximum dimension 48 of one frame substantially aligning with the axis of minimum dimension 43 and camber 45 of the other frame. Furthermore, as best seen in FIGS. 8 and 9, the cambered frame members 39 are arranged in forming the cambered fabric support structure 49 such that a support structure apex 49 is formed, the apex 49 being defined as the intersection of camber axis 45 for the cooperating frame members 39. The somewhat oversized fabric 33 indicated by dashed line in FIG. 8, has a periphery 35 sewn or otherwise affixed, as the embodiment illustrated in FIGS. 2, 6, and 7, to those portions of the frame elements 39 which form a perimeter 41 for each of the fabric support structures 37. It is again noted that the preferred fabric carried by the fabric support structures of the subject invention contributes to an occluder that has complete opposing fabric patches suspended by the cambered fabric support structures, which in turn yields a preloaded frame geometry and occluder panel arrangement that generally reduces deployment and retrieval forces while enhancing the stay flat characteristics of the device.

Although the cambered frame members which comprise the cambered fabric support structures are manufactured much like the "planar" frames of FIG. 3, namely with nitinol wire that can be wound around the pins 53 of a forming die 55 and subjected to heat treatment, during the winding process, a biasing mandrel (not shown) is used in combination with the forming die 55 to form the cambered frame member 39. Alternately, the forming die 55 itself may be contoured so as to produce a cambered frame as is depicted in FIG. 10.

As with the case of the occluder of FIGS. 1 and 2, the occluder panels are conjoined at a plurality of discrete points, the points being selected to effectively link each of the cambered fabric support structures together, as well as associate each sheet of fabric carried thereby, so as to form the variably configurable defect conforming region. With such arrangement, the resilient fabric is not only inherently or indirectly positionable in response to the defect geometry, but also directly responsive vis-a-vis the conjoined support structures.

Referring now to FIGS. 11 through 15, the general closure device 20 of the invention (i.e., those embodiments previously described) is shown being deployed to occlude a defect in a septum S. The first panel 60 (i.e., catheter side occluder panel) of the device 20 is positioned on one side of the defect while the second panel 30 is generally disposed on the other side. The frames 50 or 50A of the fabric support structures 32, 62 are elastically biased toward the position shown in FIG. 2. The defect conforming region 80 is positioned within, and expands so as to occlude the defect. Because the support structures 32, 62, vis-a-vis their frames 50 or 50A, are elastically biased toward their deployed configuration, they are biased generally toward one another and engage opposing sides of the septum about the defect. Since there are no compressive forces acting on the frames which might cause them to collapse, this serves to effectively hold the device in place and occlude the defect. The device is further shown in FIGS. 14 and 15 being retrieved from a septal defect site, as might be required in the event of inadvertent initial placement, size mismatch, or otherwise.

Figure 4:
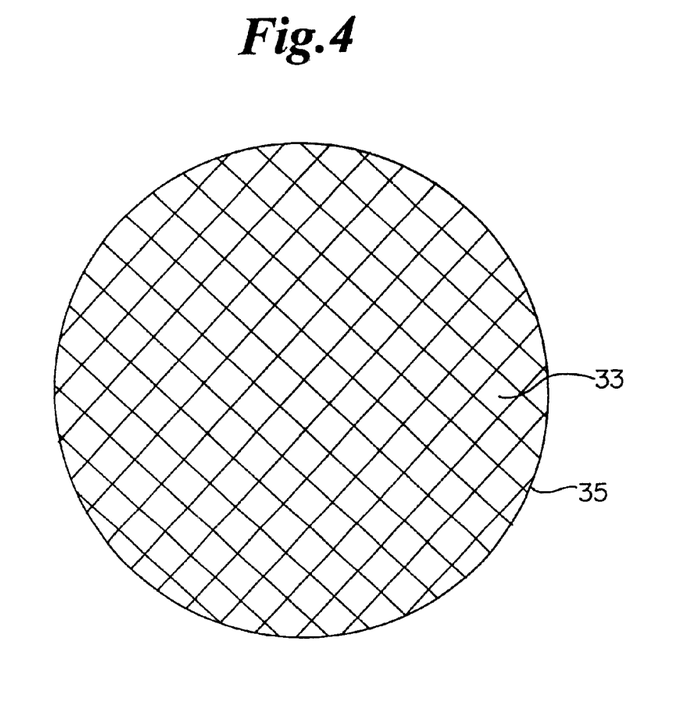
FIG. 4 depicts a fabric sheet suitable for use with the invention.

The fabric sheets 33 are formed of a relatively porous material (FIG. 4). While this may seem to contradict the purpose of the device, blood will tend to coagulate on the latticework provided by the porous material. Blood flow across the defect is usually substantially blocked after minimal time passage. If so desired, the conjoint portion of the device (or the entire device) may be treated with a thrombogenic agent to speed this natural process or may be impregnated with a biocompatible polymeric compound or the like to make it relatively impervious to fluids.

The primary purpose of using a porous fabric is to accelerate the process of permanently anchoring the device in place. The support structures hold the fabric tautly and in intimate contact with the surface of the septum S. This intimate contact between the septum and perimeter of the occluder permits ingrowth of collagen and fibrous tissue from the septum into the fabric. Over time, the membrane resting against the septum will become securely anchored to the septal wall and be covered by a layer of endothelial cells.

The design of this device is in stark contrast to the septal defect closure devices known in the art. As explained in detail above, prior art devices employ a mechanical umbrella of one design or another. The radially extending arms of the umbrella contact the septum and serve to space all but the peripheral edge of the umbrella away from the septum. Endothelial cells, collagen and fibrous tissue are therefore permitted to grow into only the very periphery of the umbrella. Thus, while a closure device of the invention essentially becomes an integral part of the septum, the complex mechanical structure of prior art devices does not enable as complete integration as the present invention.

The mechanical complexity of prior art devices also tends to markedly affect their durability. In the case of atrial or ventricular septal defects, for example, the heart obviously continues to beat after the device is in place. Since beating of the heart is accomplished by flexure of the heart muscles, the septum will flex to some degree with every beat of the heart. The radial arms must therefore flex with the septum with each and every time the heart beat. The number of cycles of this stress-inducing movement produces repeated stresses on the arms, which can eventually lead to mechanical failure and fracture of the arms.

When a closure device of the invention is deployed, the tension of the frame of the support structure opens the panel to occlude the defect. Since there are no radial arms to prop open the device, the occurrence of repeated flexion does not occur due to the beating of the heart or pressure differences between the cardiac chamber during the phase of contraction of the heart. To the contrary, any pressure difference would urge a frame and panel against the septum, more firmly occluding the defect. In addition, the superelastic material of the frame tolerates flexural stresses much better than the rigid steel arms of the prior art devices. The present device therefore will continue to flex with the septum without any significant effect on its structural integrity.

Although the foregoing has focused on application of the present invention to occlude atrial septal defects, the invention is not limited to occluding such defects. For instance, the instant closure device can be used to treat ventricular septal defects, patent ductus arteriosus, patent foramen ovale (PFO), or any other congenital or acquired orificial or tubular communications between vascular chambers or vessels.

While a preferred embodiment of the present invention has been described, it should be understood that various changes, adaptations and modifications may be made therein without departing from the spirit of the invention. Changes may be made in details, particularly in matters of shape, size, material, and arrangement of parts without exceeding the scope of the invention. Accordingly, the scope of the invention is as defined in the language of the appended claims.

What is claimed is:

1. A tissue defect occluder comprising first and second occluder panels, each occluder panel including a cambered fabric support structure and fabric suspended from a perimeter of said cambered fabric support structure, said perimeter being proximate a periphery of said fabric, said occluder panels being arranged in cooperative cambered opposition such that the perimeters of said cambered fabric support structures impart a clamping force upon tissue adjacent a tissue defect interposed therebetween when said occluder is deployed for tissue defect occlusion, said fabric support structures having dimensions and material strength characteristics so as to define a retrieval force into a catheter for said occluder of less than five pounds.

2. The occluder of claim 1 wherein the distance between the perimeter edges of the occluder panels is less than two millimeters post deployment from the catheter.

3. The occluder of claim 2 wherein the camber of said cambered fabric support structure is about 15% of a diameter of said cambered fabric support structure.

4. A tissue defect occluder comprising first and second occluder panels, each occluder panel including a cambered fabric support structure and fabric suspended from a perimeter of said cambered fabric support structure, said occluder panels being arranged in cooperative cambered opposition such that the perimeters of said cambered fabric support structures impart a clamping force upon tissue adjacent a tissue defect interposed there between when said occluder is deployed for tissue defect occlusion wherein said occluder panels are conjoined at a plurality of discrete points to thereby form a defect conforming region.

5. The occluder of claim 4 wherein said discrete conjoined points are located within each of the cambered fabric support structures, as well as on said fabric.

6. The occluder of claim 5 wherein said cambered fabric support structure includes perimeter and traversing segments.

7. The occluder of claim 6 wherein the conjoined points within the cambered fabric support structure comprise loops formed in the traversing segments of each of the cambered fabric support structures, thereby defining internal eyelets for said support structures.

8. The occluder of claim 7 wherein said internal eyelets substantially delimit said defect conforming region.

9. The occluder of claim 8 wherein the fabric of each of said cambered fabric support structures is conjoined at a single location so as to define a center fabric attachment point for said occluder.

10. The occluder of claim 9 wherein the perimeter segments of at least one of said cambered fabric support structures include loops formed therein, thereby defining perimeter eyelets for said support structure, said perimeter eyelets aiding in the symmetrical collapse of said cambered fabric support structure as during reversible retrieval of said occluder into a catheter.

11. The occluder of claim 10 wherein said internal eyelets are symmetrical about said center fabric attachment point.

12. The occluder of claim 11 wherein said fabric comprises a polymeric material.

13. The occluder of claim 12 wherein said polymeric material comprises a polyester knit.

14. The occluder of claim 12 wherein said polymeric material comprises a 20 denier polyester knit.

15. The occluder of claim 14 wherein said occluder panels are substantially round.

16. A septal defect occluder comprising first and second occluder panels, each panel including a cambered fabric support structure and fabric substantially affixed to a perimeter thereof, each of said cambered fabric support structures comprising cooperating cambered frames, the occluder panels being conjoined at internal frame points located within the perimeter of each of said cambered fabric support structures, the fabric of each of said cambered fabric support structures being joined so as to form a center fabric attachment point.

17. The occluder of claim 16 wherein each of said cooperating cambered frames has an axis of maximum dimension and an axis of minimum dimension.

18. The occluder of claim 16 wherein each of said cooperating cambered frames further has a camber axis, said camber axis being in substantial conformity with said axis of minimum dimension.

19. The occluder of claim 18 wherein said cooperating cambered frames are perpendicularly overlaying, the axis of maximum dimension of one frame substantially aligning with the axis of minimum dimension of the other frame.

20. The occluder of claim 19 wherein said internal frame points comprise loops formed in each of said cambered frames, said loops delimiting a minimum frame dimension and thereby defining internal eyelets for each of said cambered fabric support structures.

21. The occluder of claim 20 wherein the frames of one of said cambered fabric support structures comprise loops formed in said frame of one of said fabric support structures, said loops delimiting a maximum frame dimension and thereby defining perimeter eyelets for said cambered fabric support structure.

22. The occluder of claim 21 wherein said perimeter eyelets cooperatively engage means for urging said occluder from a catheter for reversible deployment in and about a septal defect site.

23. The occluder of claim 22 wherein said fabric comprises a polymeric material.

24. The occluder of claim 23 wherein said polymeric material comprises a polyester knit.

25. The occluder of claim 23 wherein said polymeric material comprises a 20 denier polyester knit.

* * * * *